(12) United States Patent
Puckett

(10) Patent No.: US 9,364,441 B2
(45) Date of Patent: Jun. 14, 2016

(54) ROTARY DIE SYSTEM

(71) Applicant: BARLEAN'S ORGANIC OILS, LLC, Ferndale, WA (US)

(72) Inventor: John Puckett, Ferndale, WA (US)

(73) Assignee: BARLEAN'S ORGANIC OILS, LLC, Ferndale, WA (US)

( * ) Notice: Subject to any disclaimer, the term of this patent is extended or adjusted under 35 U.S.C. 154(b) by 76 days.

(21) Appl. No.: 14/286,850

(22) Filed: May 23, 2014

(65) Prior Publication Data

US 2014/0348934 A1 Nov. 27, 2014

Related U.S. Application Data

(60) Provisional application No. 61/826,897, filed on May 23, 2013.

(51) Int. Cl.

| | | |
|---|---|---|
| *A61K 9/48* | (2006.01) | |
| *A61J 3/07* | (2006.01) | |
| *B29C 33/42* | (2006.01) | |
| *B65B 43/60* | (2006.01) | |
| *A61J 3/00* | (2006.01) | |
| *A61K 9/20* | (2006.01) | |
| *A61K 9/28* | (2006.01) | |

(52) U.S. Cl.
CPC .............. *A61K 9/4833* (2013.01); *A61J 3/005* (2013.01); *A61K 9/2072* (2013.01); *A61K 9/2873* (2013.01); *A61K 9/2893* (2013.01); *A61K 9/4825* (2013.01); *Y10T 156/103* (2015.01); *Y10T 156/1378* (2015.01)

(58) Field of Classification Search
None
See application file for complete search history.

(56) References Cited

U.S. PATENT DOCUMENTS

| | | |
|---|---|---|
| 2,522,154 A | 9/1950 | Asmussen |
| 3,038,282 A | 6/1962 | Hansen |
| 4,026,437 A | 5/1977 | Biddle |
| 4,594,926 A * | 6/1986 | Propheter ............... B26F 1/04 83/345 |
| 5,146,730 A | 9/1992 | Sadek |
| 5,535,885 A | 7/1996 | Daniel |
| 5,761,886 A | 6/1998 | Parkhideh |
| 5,827,535 A | 10/1998 | Stone |
| 6,183,845 B1 | 2/2001 | Ikemoto |
| 6,482,516 B1 | 11/2002 | Sadek |
| 7,490,456 B2 * | 2/2009 | Draisey .................. A61J 3/07 53/454 |
| 8,621,764 B2 | 1/2014 | Puckett |
| 2004/0253312 A1 * | 12/2004 | Sowden ................ A23G 3/04 424/473 |
| 2006/0292217 A1 | 12/2006 | Schmidt |
| 2007/0212411 A1 | 9/2007 | Fawzy |
| 2008/0057115 A1 | 3/2008 | Okamoto |
| 2008/0295751 A1 * | 12/2008 | Shoup ................... A01C 7/081 111/174 |
| 2009/0208608 A1 | 8/2009 | Emerson |
| 2014/0072625 A1 | 3/2014 | Chidambaram |

FOREIGN PATENT DOCUMENTS

| | | |
|---|---|---|
| WO | 2007103557 | 9/2007 |
| WO | 2014190324 A2 | 11/2014 |

OTHER PUBLICATIONS

International Search Report and Written Opinion issued on Nov. 19, 2014 for PCT/US2014/039446.
International Search Report and Written Opinion issued Feb. 18, 2016 in PCT/US2015/057964 (13 Pages).
International Preliminary Report on Patentability issued Nov. 24, 2015 in PCT/US2014/039446 (7 Pages).
NonFinal Rejection issued in U.S. Appl. No. 14/926,217 on Jan. 4, 2016 (12 pages).
Invitation to Pay Additional Fees issued Dec. 18, 2015 in PCT/US2015/057964 (2 pages).

* cited by examiner

*Primary Examiner* — H. Sarah Park
(74) *Attorney, Agent, or Firm* — Jason M. Pass

(57) ABSTRACT

A rotary die system that includes first and second axially aligned, coacting rotary dies positioned adjacent one another. Each die includes a working surface having a plurality of recesses defined therein. The recesses in the first die are each configured to align with a recess in the second die to form a product cavity upon coaction of the first and second dies. The product cavity is configured to receive a product. Each recess in at least one of the first or second dies includes a pin therein that is configured to puncture a film that at least partially surrounds the product.

20 Claims, 3 Drawing Sheets

ROTARY DIE SYSTEM

CROSS REFERENCE TO RELATED APPLICATIONS

This application claims the benefit of U.S. Provisional Application No. 61/826,897 filed May 23, 2013, which is incorporated herein by reference in its entirety.

FIELD OF THE INVENTION

The present invention relates to a compressed tablet or caplet having gelatin with an opening therein added to the outside surface thereof with a rotary die system.

BACKGROUND OF THE INVENTION

The pharmaceutical, vitamin and related industries have long used various ways to present their products to users in swallowable oral dosage forms, other than purely as liquids, so that persons using such products can use them conveniently and comfortably. Broadly, orally used non-liquid medicines and the like are provided in two general forms. One form is a tablet in which the dosage unit is a solid, hard swallowable shape comprised of the desired active ingredients compressed and formed with suitable binders into an integral article. Tablets, in their broadest sense, are available in many shapes and sizes. The other common solid dosage is a capsule in which the active ingredients occur in a flowable state (powder, liquid, paste or the like) and are encased in a digestible shell of a suitable shape and form which is swallowable. Variations exist within and between these two general forms. Thus, it is known to coat, as by dipping or spraying, tablet-type dosage units with gelatin or other materials to make them more palatable, easier to swallow, less prone to powder or to flake when handled in bottles, colored for eye appeal or identifiability, and longer lasting before active ingredients degrade, among other reasons. Capsule forms of such products occur as soft gelatin capsules, which commonly are of spherical or oblate spherical shape, and as hard gelatin capsules which commonly are of elongated round-ended cylindrical form and which are made in two pieces for assembly, with or without sealing, around the flowable fill material containing the desired active ingredients. See, for example, U.S. Pat. No. 6,482,516 to Sadek, U.S. Pat. No. 5,146,730 to Sadek and U.S. Publication No. 2014/0072625 to Chidambaram, the entireties of which are incorporated herein by reference. The membrane or coating is present to protect the inner materials and aid in consumption. However, it is advantageous for the membrane and product therein to digest quickly.

SUMMARY OF THE PREFERRED EMBODIMENTS

In accordance with a first aspect of the present invention there is provided a rotary die system that includes first and second axially aligned, coacting rotary dies positioned adjacent one another. Each die includes a working surface having a plurality of recesses defined therein. The recesses in the first die are each configured to align with a recess in the second die to form a product cavity upon coaction of the first and second dies. The product cavity is configured to receive a product. Each recess in at least one of the first or second dies includes a pin therein that is configured to puncture a film that at least partially surrounds the product. In a preferred embodiment, each recess in the first and second dies includes a pin therein that is configured to puncture a film that at least partially surrounds the product. Preferably, each pin is movable between a retracted position and a deployed position. The pins are configured to puncture the film that at least partially surrounds the product in the deployed position. Preferably, the the pins are movable between the retracted position and the deployed position by gravity.

In a preferred embodiment, the rotary die system further includes a hopper that has an open top and a bottom, and a sorter that has a top and a bottom. The sorter is positioned at the bottom of the hopper, and the sorter is configured to feed product between the first and second dies. Preferably, the rotary die system also includes at least one vacuum return tube that has first and second ends. The first end includes a return opening therein that is positioned adjacent the top of the sorter and the second end is positioned adjacent the top of the hopper. The vacuum return tube is configured to move excess products accumulated at the top of the sorter back to the top of the hopper via a vacuum. In a preferred embodiment, the rotary die system also includes an overflow brush or plug that is movable between a plugged position where it blocks the return opening and the vacuum, and an unplugged position where it does not block the return opening and the vacuum, thus allowing excess products to be moved via the vacuum from the top of the sorter back to the top of the hopper. Preferably, the overflow brush is movable from the plugged to the unplugged position by excess products positioned at the top of the sorter.

In accordance with another aspect of the present invention there is provided a method of providing an enrobed product that includes providing first and second films, providing first and second axially aligned, coacting rotary dies positioned adjacent one another, and moving the films through a place of coaction of the first and second dies. The first and second dies include cooperating working surfaces that include a plurality of recesses defined therein that form between them, upon coaction of the dies, at least a first cavity for receiving therein a product. The method includes dispensing a product into contact with at least one of the first and second films at a location on the at least one film that corresponds to the location of the first cavity, at the place of die coaction, stretching the first and second films around the product to cause the product to be enrobed by and between the first and second films, puncturing at least one of the first and second films while the product is located in the cavity, and separating the enrobed product from the first and second films. Preferably, the puncturing step is performed by a pin that is movable between a retracted position and a deployed position.

In a preferred embodiment, the method includes providing a hopper having an open top and a bottom, and a sorter having a top and a bottom that is positioned at the bottom of the hopper. The sorter is configured to feed product between the first and second dies. The method includes placing a plurality of products into the hopper that fall into the sorter, and vacuuming at least one excess product from adjacent the top of the sorter back to the top of the hopper. In a preferred embodiment, the method includes moving an overflow brush from a plugged position to an unplugged position prior to the step of vacuuming at least one excess product from adjacent the top of the sorter back to the top of the hopper.

In accordance with another aspect of the present invention there is provided an enrobed product that includes a product, and first and second gelatin coating portions enrobing the product that are sealed together along a seal line encircling the product. At least one of the first and second coating portions includes an opening defined therein that exposes the product.

Preferably, both the first and second coating portions include an opening defined therein that exposes the product.

The invention, together with additional features and advantages thereof, may be best understood by reference to the following description.

BRIEF DESCRIPTION OF THE DRAWINGS

Like numerals refer to like parts throughout the several views of the drawings.

DETAILED DESCRIPTION OF THE PREFERRED EMBODIMENTS

Figure 1:
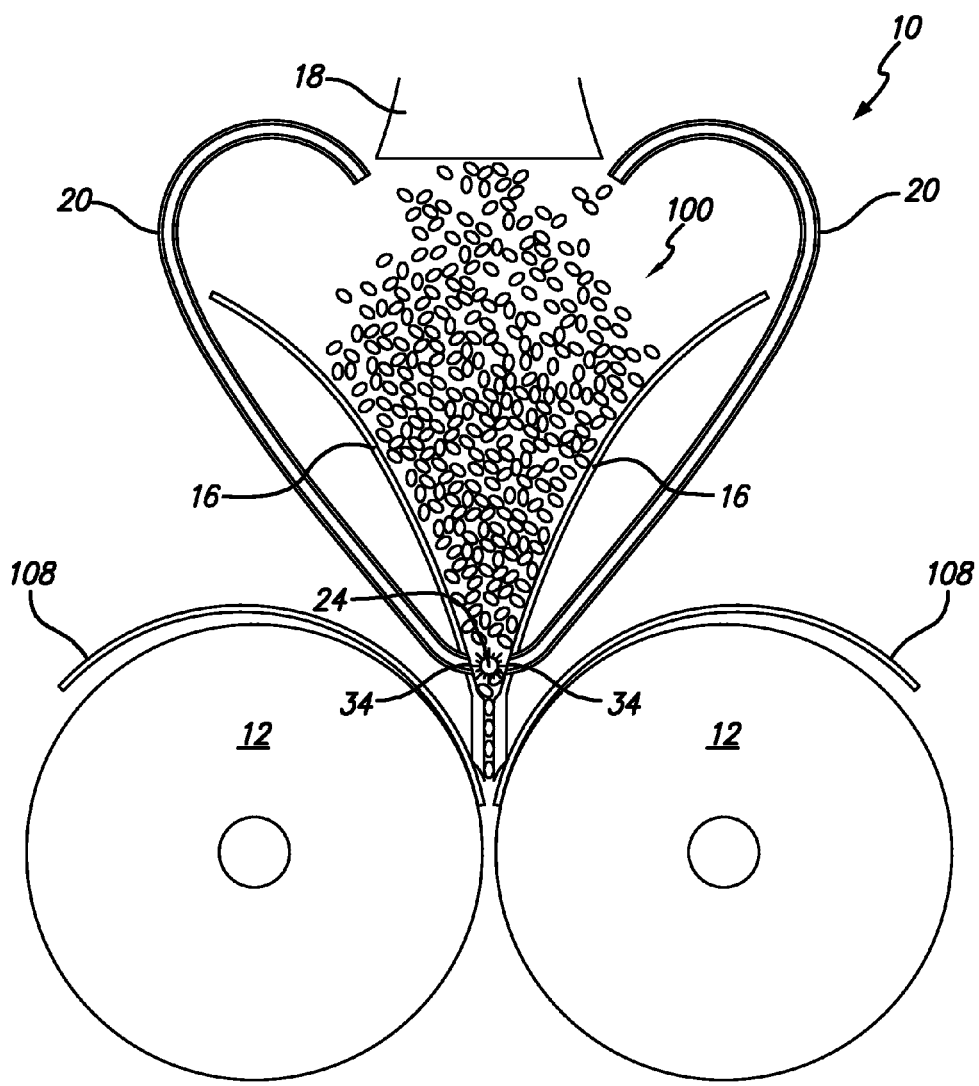
FIG. 1 is a schematic view of a rotary die system in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an other embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

In broad terms, this invention concerns the coating of tablets, other solid dosage forms, and a variety of solids by enrobement with films of gelatin or other sealable polymers by an enrobement process which uses coacting die techniques in which the tablets or other articles to be enrobed are introduced individually between two sealable films positioned between opposing matching dies configured to cause the films to stretch and deform around each introduced article so that the films move into contact with each other, are sealed to each other and, as sealed, are severed from the film webs to provide individual film-enrobed end products. The particular product which formed the focus of the development of this invention is a tablet of caplet configuration enrobed between applied gelatin films which adhere to the solid tablet product to produce a non-peelable, tamper-evident and potentially tamper-resistant gelatin coated caplet-type medicine tablet.

The hermetically-sealed applied-film coating around the tablet or other solid core of the enrobed product can be treated after production for controlled release or enteric release. Due to the continuous nature of the applied-film coating, individual coated units provide an assurance of consistent product performance.

In the following description, unless the usage context indicates otherwise, the term "tablet" is used in its broad sense to mean a solid, hard, unitary pellet containing one or more active ingredients, which pellet is of such size as to be administered by an intended user and is of desired geometry; the term includes such things having caplet configuration, which things are often referred to simply as "caplets".

FIGS. 1-5 show a rotary die system 10 that provides a compressed tablet or caplet 100 having a gelatin coating 102 thereon and that includes at least one opening 104 in the coating. Generally, the material (e.g., tablet or caplet) that is enrobed by the gelatin coating 102 is referred to herein as the "product" 100 and the product together with the gelatin coating 102 is referred to herein as the enrobed product 106. The enrobed product 106 (best shown in FIG. 5) includes the product and a hard gelatin coating 102 that fully encloses the product 100. The gelatin coating 102 conforms tightly to the contours of the product 100 and is adhered tightly to the surfaces of the product 100 over the entire exterior thereof. The gelatin coating 102 is comprised of preferably first and second coating portions 102a and 102b of soft elastic gelatin that are applied to opposite sides of the product 106, each include an opening 104 therein, and are sealed together, in an essentially edge-to-edge manner, along a seal line 107 that encircles the product 100 to create the enrobed product 106.

As shown in FIG. 1, in a preferred embodiment, the rotary die system 10 generally includes first and second dies 12 that are each configured to rotate about an axis, a hopper 16, a filler 18, a plurality of vacuum return tubes 20, a sorter 22 and an overflow brush 24. Generally, the products 100 are dispensed from the filler 18 and fall into the hopper 16 and are gravity fed to the sorter 22, which is positioned at the bottom of the hopper 16. After being sorted by the sorter 22, the products 100 is dispensed on a self-timed basis into essentially simultaneous contact with two enrobing gelatin films or sheets 108 that are supported on the locally recessed coacting rotary dies 12. The films 108 deform around each product 100 and are sealed by the dies 12 to each other before the dies coact to cut the enrobed products 106 from the films 108. In the presently preferred embodiments of the manufacturing process and system described herein, the product feeding mechanism (e.g., hopper 16 and sorter 22) is arranged to introduce the products 100 to the films 108 in the working area between the dies 12 so that each product 100 contacts both films 108 essentially simultaneously.

Figure 3:
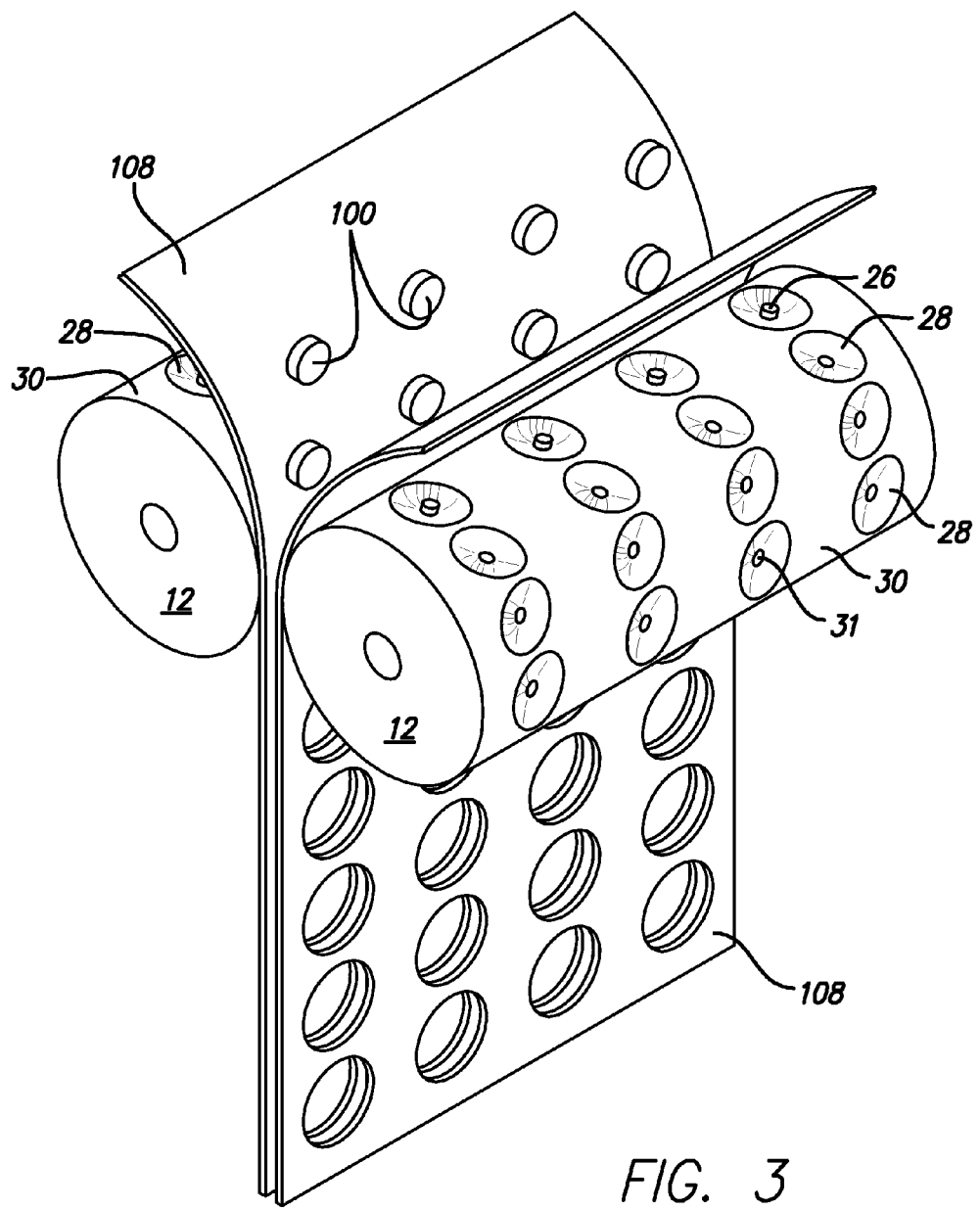
FIG. 3 is a perspective view of the rotary die system of FIG. 1.
Figure 4:
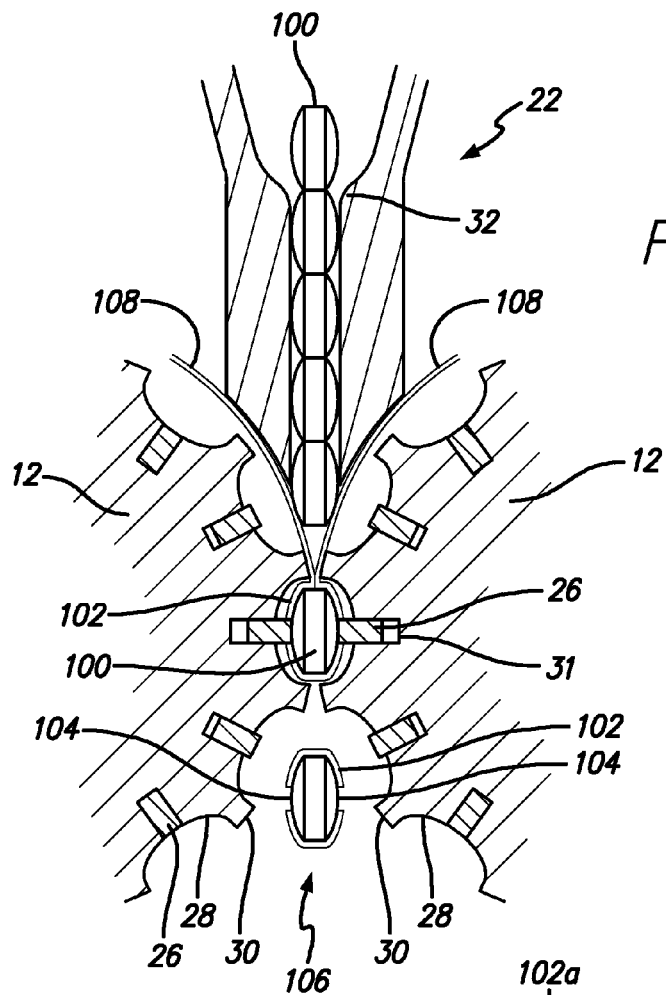
FIG. 4 is a cross-sectional view taken along line 4-4 of FIG. 1.
Figure 5:
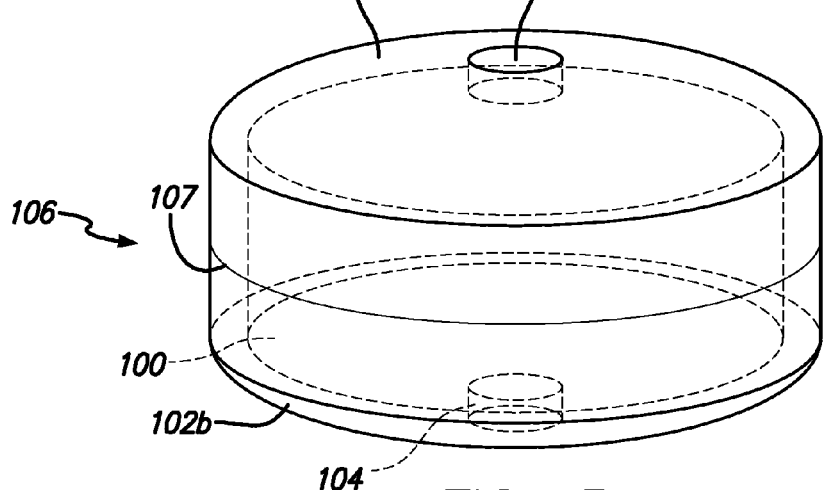
FIG. 5 is a perspective view of an enrobed product in accordance with a preferred embodiment of the present invention.

As shown in FIGS. 3-4, in a preferred embodiment, the first and second dies 12 include a plurality of pins 26 that are positioned in recesses 28 that are defined in an outer working surface 30 of each of the dies 12. In use, the pins 26 prick the film 108 and provide an opening 104 in resulting coating 102 in the enrobed product 106, as shown in FIG. 5. It will be appreciated that each of the recesses 28 in the working surface 30 of a die 12 cooperates with a corresponding recess 28 in the other die 12 for defining a corresponding cavity between the dies 12 as they turn about their axes of rotation into and out of substantially matching coaction with each other. The cavities defined by cooperation of the respective recesses 28 are sized and shaped to loosely receive in each cavity a single product 100.

In a preferred embodiment, each pin 26 is movable between a retracted or first position, where the pin 26 is retracted into the die 12, and a deployed or second position, where the pin 26 is in position to prick the film 108 to form opening 104. In a preferred embodiment, the pins 26 are movable between the retracted and deployed positions via gravity. In another embodiment, the pins can be deployed via centrifugal force. In the retracted position, the pins 26 are positioned in openings 31 at the bottom of each recess 28. In use, as the dies rotate the pin 26 pushes through the gelatin 102 to produce the opening 104. In a preferred embodiment, as the gelatin 102 dries the opening 104 expands due to the loss of moisture in the gelatin 102.

Figure 2:
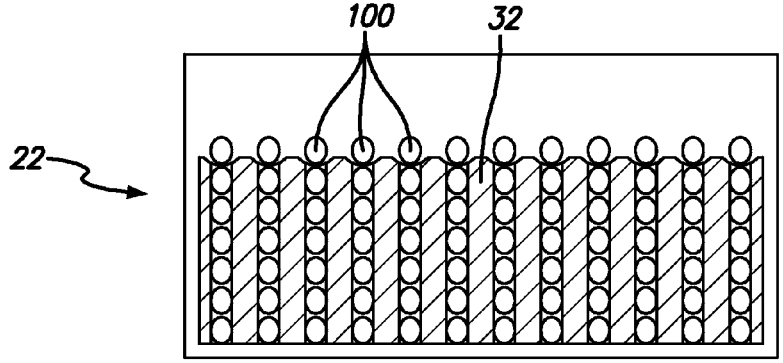
FIG. 2. is a front elevational view of a sorter that is part of the rotary die system of FIG. 1.

In a preferred embodiment, the die system 10 includes the vacuum return tubes 20, and overflow brush 24, as discussed above. During processing there may at times be an excess overflow of products 100 into the hopper 16 and to the sorter 22. Essentially, there may be a point where the sorter 22 cannot handle the amount of products 100. The sorter 22 preferably includes a manifold 32. To prevent clogging of the manifold 32, the overflow brush 24 and vacuum return tubes 20 cooperate to move products 100 from the bottom of the hopper 16 back to the top. FIG. 2 shows the sorter 22 full of products 100. If more products 100 come down on top of the full sorter 22, the overflow brush 24 is pushed upwardly, which unblocks the vacuum return tubes 20 (see return openings 34). Essentially, overflow brush 24 acts as a plug. Therefore, once overflow brush 24 is moved upwardly, the vacuum within vacuum return tubes 20 pulls the excess products 100 through the tubes and reenters the products 100 into the top of the hopper 16.

FIG. 5 shows an enrobed product 106, that includes openings 104 in the coating 102 on the outside thereof. It will be appreciated by those of ordinary skill in the art that when a person ingests the enrobed product 106 and the acid in the stomach enters the opening 104 and reaches the product 100, the product 100 expands and the gelatin 102 ruptures. In an exemplary embodiment, this allows for the product 100 to be released within about ten minutes of ingestion.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A rotary die system comprising:
    first and second axially aligned, coacting rotary dies positioned adjacent one another,
    wherein each die comprises a working surface having a plurality of recesses defined therein,
    wherein each recess in the first die is configured to align with a recess in the second die to form a product cavity upon coaction of the first and second dies,
    wherein the product cavity is configured to receive a product,
    wherein each recess in at least one of the first or second dies comprises a pin therein, the pin being movable between a retracted position and a deployed position by gravity and being configured to puncture a film that at least partially surrounds the product in the deployed position.

2. The rotary die system of claim 1, wherein each recess in the first and second dies comprises a pin therein that is configured to puncture the film that at least partially surrounds the product.

3. The rotary die system of claim 2, wherein each pin is movable between a retracted position and a deployed position and wherein each pin is configured to puncture the film that at least partially surrounds the product in the deployed position.

4. The rotary die system of claim 1, further comprising a hopper having an open top and a bottom, and a sorter having a top and a bottom, wherein the sorter is positioned at the bottom of the hopper, and wherein the sorter is configured to feed product between the first and second dies.

5. The rotary die system of claim 4, further comprising at least one vacuum return tube having first and second ends, wherein the first end comprises a return opening therein that is positioned adjacent the top of the sorter and the second end is positioned adjacent the top of the hopper, and wherein the vacuum return tube is configured to move excess products accumulated at the top of the sorter back to the top of the hopper via a vacuum.

6. The rotary die system of claim 5, further comprising an overflow brush that is movable between a plugged position in which the overflow brush blocks the return opening and the vacuum, and an unplugged position in which the overflow brush does not block the return opening and the vacuum, thus allowing excess products to be moved via the vacuum from the top of the sorter back to the top of the hopper.

7. The rotary die system of claim 6, wherein the overflow brush is movable from the plugged to the unplugged position by excess products positioned at the top of the sorter.

8. A rotary die system comprising:
    first and second axially aligned, coacting rotary dies positioned adjacent one another, wherein each die comprises a working surface, the working surface of the first die comprising a first recess disposed thereon and the working surface of the second die comprising a second recess disposed thereon, wherein the first recess in the first die is configured to align with the second recess in the second die to form a product cavity for receiving a product upon coaction of the first and second dies; and
    a first pin positioned therein the first recess that is configured to puncture a film that at least partially surrounds the product, wherein the first pin is movable between a retracted position and a deployed position by gravity and wherein the first pin is configured to puncture the film that at least partially surrounds the product in the deployed position.

9. The rotary die system of claim 8, further comprising a second pin positioned therein the second recess that is configured to puncture the film that at least partially surrounds the product.

10. The rotary die system of claim 9, wherein the second pin is movable between a retracted position and a deployed position by gravity.

11. The rotary die system of claim 10, wherein the second pin is configured to puncture the film that at least partially surrounds the product in the deployed position.

12. The rotary die system of claim 8, further comprising a hopper having an open top and a bottom, and a sorter having a top and a bottom, wherein the sorter is positioned at the bottom of the hopper, and wherein the sorter is configured to feed product between the first and second dies.

13. The rotary die system of claim 12, further comprising at least one vacuum return tube having first and second ends, wherein the first end comprises a return opening therein that is positioned adjacent the top of the sorter and the second end is positioned adjacent the top of the hopper, and wherein the vacuum return tube is configured to move excess products accumulated at the top of the sorter back to the top of the hopper via a vacuum.

14. The rotary die system of claim 13, further comprising an overflow brush that is movable between a plugged position in which the overflow brush blocks the return opening and the vacuum, and an unplugged position in which the overflow brush does not block the return opening and the vacuum, thus allowing excess products to be moved via the vacuum from the top of the sorter back to the top of the hopper.

15. The rotary die system of claim 14, wherein the overflow brush is movable from the plugged to the unplugged position by excess products positioned at the top of the sorter.

16. A rotary die system comprising:
    first and second axially aligned, coacting rotary dies positioned adjacent one another, each die comprising a working surface having a plurality of recesses defined therein,
        wherein each recess in the first die is configured to align with a recess in the second die to form a product cavity for receiving a product upon coaction of the first and second dies, and
        wherein each recess in at least one of the first or second dies comprises a pin therein that is configured to puncture a film that at least partially surrounds the product;
    a hopper having an open top and a bottom, and a sorter having a top and a bottom, wherein the sorter is positioned at the bottom of the hopper, and wherein the sorter is configured to feed product between the first and second dies;

at least one vacuum return tube having first and second ends, wherein the first end comprises a return opening therein that is positioned adjacent the top of the sorter and the second end is positioned adjacent the top of the hopper, and wherein the vacuum return tube is configured to move excess products accumulated at the top of the sorter back to the top of the hopper via a vacuum; and an overflow brush that is movable between a plugged position in which the overflow brush blocks the return opening and the vacuum, and an unplugged position in which the overflow brush does not block the return opening and the vacuum, thus allowing excess products to be moved via the vacuum from the top of the sorter back to the top of the hopper.

17. The rotary die system of claim 16, wherein the overflow brush is movable from the plugged to the unplugged position by excess products positioned at the top of the sorter.

18. The rotary die system of claim 16, wherein the pin in at least one of the first or second dies is movable to a deployed position by centrifugal force.

19. The rotary die system of claim 16, wherein the first pin is movable between a retracted position and a deployed position by gravity.

20. The rotary die system of claim 18, wherein the pin in at least one of the first or second dies is configured to puncture the film that at least partially surrounds the product in the deployed position.

* * * * *